United States Patent [19]

Hatanaka et al.

[11] Patent Number: 4,749,868

[45] Date of Patent: Jun. 7, 1988

[54] METHOD OF PROCESSING A SAMPLE CONTAINING WATER UNDER SCANNING ELECTRON MICROSCOPE AND APPARATUS THEREOF

[75] Inventors: Masayoshi Hatanaka; Tadayuki Uekita, both of Iwaki, Japan

[73] Assignee: Kureha Chemical Industry Company Limited, Tokyo, Japan

[21] Appl. No.: 916,618

[22] Filed: Oct. 8, 1986

[30] Foreign Application Priority Data

Oct. 11, 1985 [JP] Japan .................... 60-226096

[51] Int. Cl.$^4$ .................................. G21K 5/08
[52] U.S. Cl. ........................... 250/443.1; 250/442.1
[58] Field of Search ............... 250/441.1, 442.1, 443.1

[56] References Cited

U.S. PATENT DOCUMENTS 3,761,709 9/1973 Hasegawa et al. ............ 250/441.1
3,958,124 5/1976 Koch et al. ................... 250/442.1
4,227,080 10/1980 Okura et al. .................. 250/442.1

OTHER PUBLICATIONS

Andersson et al, A Combined Vacuum Interlock and Preparation Assembly for MBE and Surface Analysis, J. Phys. E., vol. 16, 1983, pp. 364–366.

Primary Examiner—Carolyn E. Fields
Assistant Examiner—John A. Miller
Attorney, Agent, or Firm—Koda and Androlia

[57] ABSTRACT

Useful fragments such as hyphae are extracted from a raw sample containing water such a fungi attached to a plant. The sample is rapidly frozen and cut under vacuum largely and at random. Water contained in the sample is sublimated and the sample is coated with conductive material. While observing the sample by a scanning electron microscope, useful fragments are extracted from the sample by a micro-manipulator.

2 Claims, 7 Drawing Sheets

FIG.3A
FIG.3B
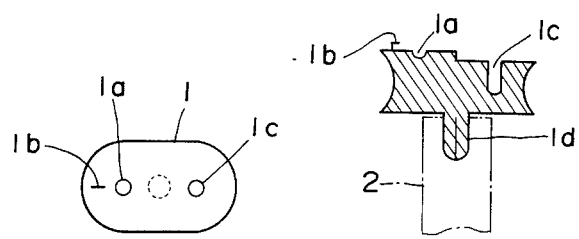
FIG.4
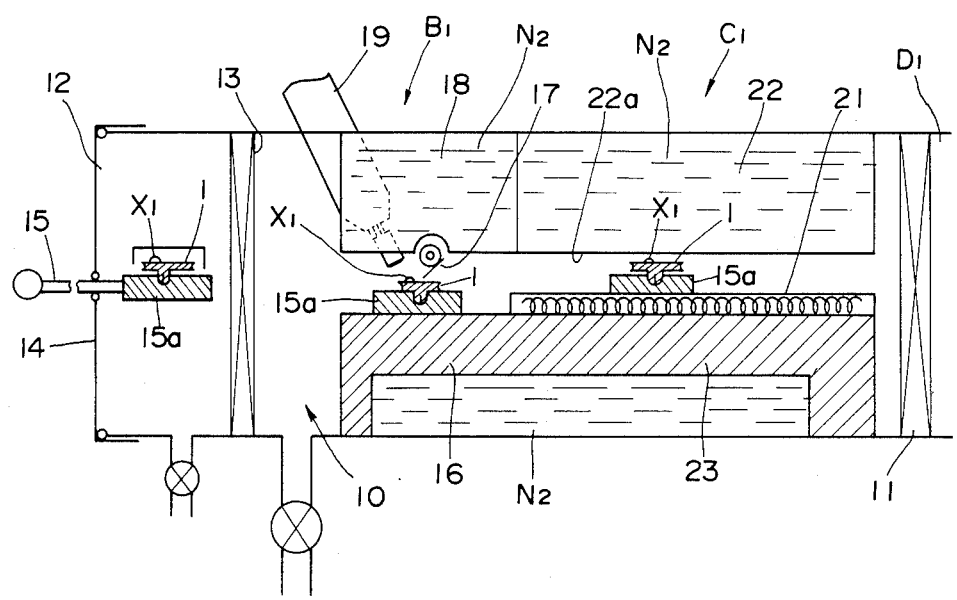

METHOD OF PROCESSING A SAMPLE CONTAINING WATER UNDER SCANNING ELECTRON MICROSCOPE AND APPARATUS THEREOF

BACKGROUND OF THE INVENTION

1. Field of the Invention

The present invention relates to a method of processing a sample containing water by micro-manipulator under a scanning electron microscope and an apparatus thereof, and more particularly, to such a sample treatment method under a scanning electron microscope in which a raw sample containing water is cut while being observed by a scanning electron microscope to extract useful fragments from the sample and an apparatus thereof.

2. Prior Art

In recent applications of the biology, it is desirable to develop the technique for use in various studies in which minute useful fragments are extracted from a raw sample to culture them. For example, hyphae are extracted from a certain species of fungi attached to a plant and a high degree of analysis is made to the hyphae, or hyphae are extracted from a certain species of mold and hyphae are cultured.

Since useful fragments extracted from the sample such as fungi are very minute, it is necessary to use an electron microscope in order to observe the fragments. Operation required for conventional studies of this kind include cutting, for example, a plant containing fungi at random or sectioning thinly the plant, observing the cut segments by a scanning electron microscope and/or a transmission electron microscope and searching the segments for useful fragments to be extracted. In such a conventional manner, however, it must be waited that useful fragments, for example, hyphae are detected accidentally from the cut segments obtained from the sample cut at random. Further, even if the useful fragments are detected, it is technically difficult to extract the fragments effectively. Accordingly, the conventional observation required to extract the useful fragments from the sample is very inefficient and it is almost impossible to extract many minute useful fragments, for example, hyphae from the sample such as a plant constantly. Therefore, in the serious study of the biology applications, the scanning electron microscope can not be sufficiently utilized for operation, for example, extraction of part of the sample other than observation. The similar problem exists in operation of extracting minute segments from high molecules in the state containing water or solvent.

SUMMARY OF THE INVENTION

It is an object of the present invention to provide a sample processing method capable of extracting useful fragments such as hyphae from a raw sample containing water such a fungi attached to a plant exactly without error.

It is another object of the present invention to provide a sample processing method in which a raw sample containing water such as fungi attached to a plant is moved on a cooling stage in a scanning electron microscope without change in quality to the utmost so that the sample can be observed by the microscope and useful fragments can be extracted exactly from the sample under observation by the microscope.

It is a further object of the present invention to provide an apparatus in which the steps of cutting a raw sample containing water, sublimating water contained in the cut sample and extracting useful fragments by a manipulator are made as a series of processes in a vacuum chamber.

BRIEF DESCRIPTION OF THE DRAWINGS

FIG. 3A is a plan view of a holder of a sample;

FIG. 3B is a longitudinal sectional view of the holder of FIG. 3A;

FIG. 4 is a longitudinal sectional view of a vacuum chamber in which a frozen sample is cut and water contained in the sample is sublimated;

DETAILED DESCRIPTION OF THE INVENTION

A structure of an apparatus for processing a sample containing water under a scanning electron microscope is now described.

Figure 2:
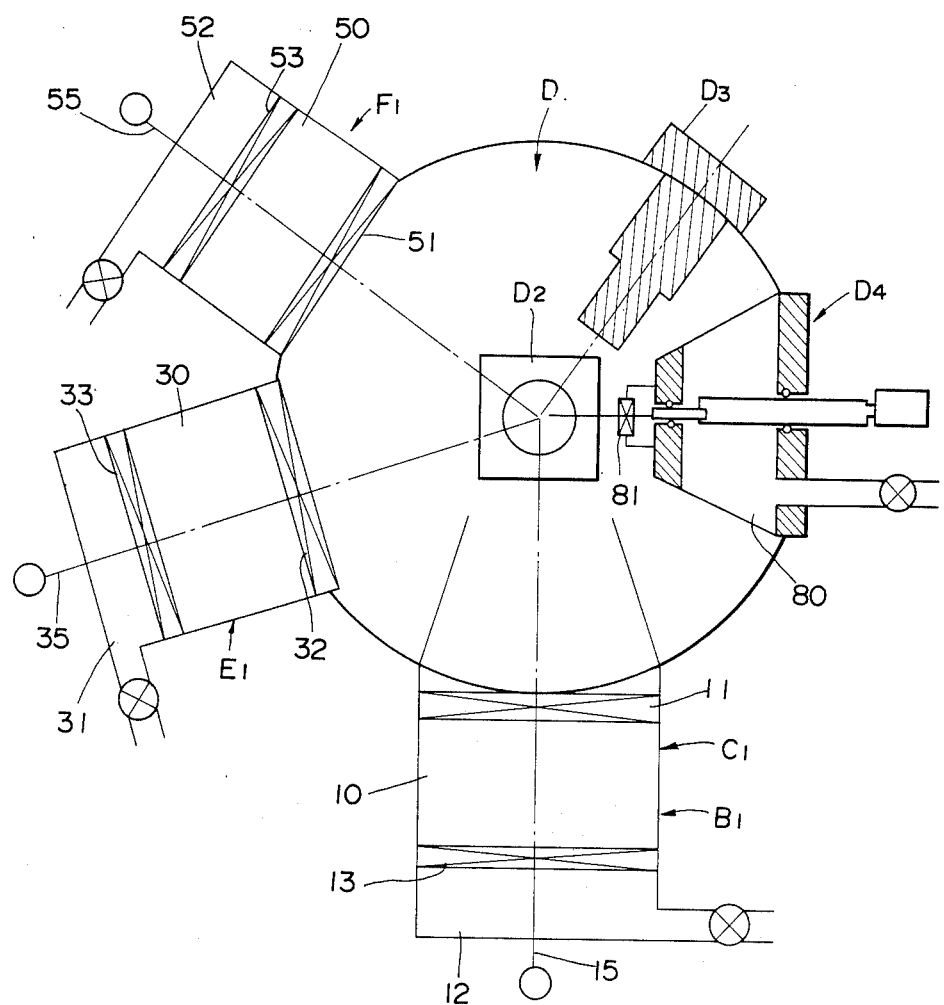
FIG. 2 is a sectional view in plan showing an apparatus according to the present invention in which vacuum chambers used in each process are disposed around an operation chamber of a scanning electron microscope.

Referring to FIG. 2, there is shown the scanning electron microscope having an operation chamber $D_1$ and a cooling stage $D_2$ disposed in a center of the chamber $D_1$. The microscope is provided with a secondary-electron detector $D_3$. Disposed around the operation chamber $D_1$ are a vacuum chambers $B_1$ for cutting a frozen sample, a vacuum chamber $C_1$ for sublimating water contained in a sample, a vacuum chamber $E_1$ for processing a sample under an optical microscope, a vacuum chamber $F_1$ for coating conductive material on a sample and an operation chamber $D_4$ for use with a micro-manipulator. The vacuum chambers $B_1$ and $C_1$ are in the sample vacuum chamber.

FIGS. 3A and 3B show a holder 1 of a sample. The holder 1 is provided with a groove or hole $1a$ in which a sample is placed, a needle $1b$ which holds the sample and a container $1c$ in which useful fragments extracted from the sample are contained. When the sample is a suspension containing fungi, the suspension is held on the groove $1a$ by the surface tension thereof. When the sample is part of a plant, the sample is held down by the needle $1b$. The holder 1 is formed at its bottom with a chucking projection $1d$. The projection $1d$ of the holder 1 is held by a holding member 2 shown by one-dot chain line in FIG. 3B, and the sample placed on the holder 1 is rapidly frozen in a rapid freezing process A (refer to FIG. 1). An actual method of the rapid freezing process A is carried out by rapidly immersing the holder 1 into liquid nitrogen. The holder 1 holding the rapidly frozen sample is moved in the vacuum chambers $B_1$ to $F_1$ shown in FIG. 2 so that the sample is subjected to various processes in the vacuum chambers.

An actual structure of the vacuum chambers $B_1$ to $F_1$ is now described.

FIG. 4 shows a structure of the vacuum chambers $B_1$ and $C_1$. Both the chambers are disposed in a common vacuum chamber 10. The vacuum chamber 10 is maintained to a high vacuum of about $10^{-10}$ to $10^{-11}$ torr. The vacuum chamber 10 communicates with the operating chamber $D_1$ of the canning electron microscope through a gate valve 11 disposed at the right of FIG. 4. A preliminary exhaust chamber 12 is disposed at the left of the vacuum chamber 10 and is separated from the chamber 10 by a gate valve 13. The preliminary exhaust chamber 12 is maintained to a low vacuum of about $10^{-2}$ torr.

The chamber 12 is closed by a cover 14, and a rod 15 which is used to move a sample is inserted into the chamber 12 through the cover 14. The holder 1 is held on a table 15a which is detachably coupled with an end of the rod 15.

The vacuum chamber $B_1$ comprises a cooling block 16, a cutter 17 which cuts a frozen sample roughly and a cooling chamber 18 which cools the cutter 17. The cooling block 16 is filled with liquid nitrogen $N_2$. The table 15a is placed on the cooling block 16. The cutter 17 may be a type of rotating about a horizontal axis or a type of rotating about a vertical axis and is adapted to cut a frozen sample $X_1$ on the holder 1 manually. The cooling chamber 18 is filled with liquid nitrogen $N_2$ and the cutter 17 is maintained to a low temperature. An optical microscope 19 of the low magnification is disposed above the holder 1. The cut frozen sample $X_1$ can be observed by the optical microscope.

The vacuum chamber $C_1$ comprises a heating member 21 disposed on the cooling block 16 and a cooling chamber 22 for sublimation disposed above the heating member 21 oppositely thereto. The heating member 21 contains a heater 23 therein and can heat the holder 1 gradually. The cooling chamber 22 is filled with liquid nitrogen $N_2$. The cooling chamber 22 includes an external lower surface forming a sublimation surface 22a plated with gold. The table 15a is placed on the heating member 21 and the frozen sample $X_1$ placed on the table 15a is opposed to the sublimation surface 22a with a small gap being formed between the sample $X_1$ and the sublimation surface 22a. The sample $X_1$ is gradually heated by the heater 23 so that water contained in the frozen sample $X_1$ is sublimated from the cut surface thereof.

It is desirable that the sublimation process is performed while moving gradually the table 15a to the right in the drawing. In order to finely adjust the distance between the frozen sample $X_1$ and the sublimation surface 22a, the heating member 21 may be finely moved up and down. If there is a case in which a sample which does not require the sublimation process is processed, the vacuum chamber $C_1$ may be formed in a structure in which the heating member 21 can be removed.

Figure 5:
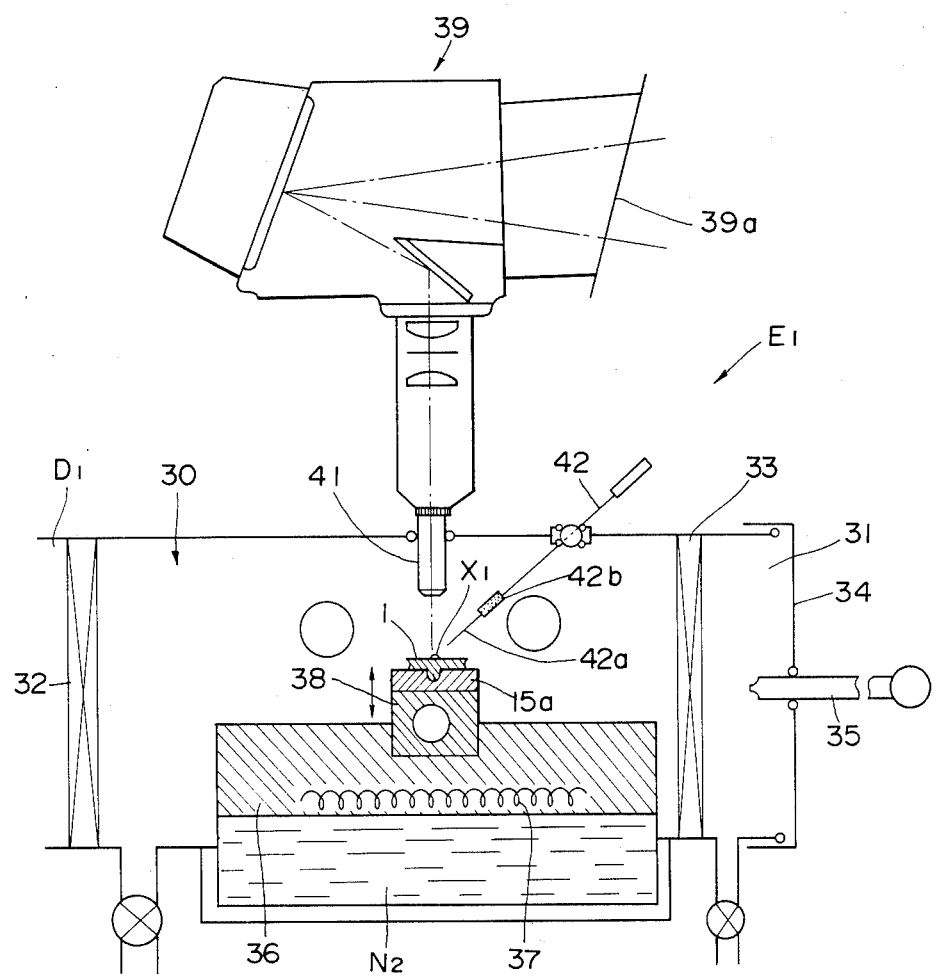
FIG. 5 is a longitudinal sectional view of a vacuum chamber in which a sample is processed under an optical microscope.

FIG. 5 shows a structure of the vacuum chamber $E_1$ which is used to perform the process of processing a sample under the optical microscope. The vacuum chamber $E_1$ is used to observe the sample sublimated in the vacuum chamber $C_1$ with low magnification and to cut the sample into more minute segments if necessary. The vacuum chamber $E_1$ includes a vacuum chamber 30 and a preliminary exhaust chamber 31. The vacuum chamber 30 is separated from the operation chamber $D_1$ of the scanning electron microscope by a gate valve 32 and is also separated from the preliminary exhaust chamber 31 by a gate valve 33. The preliminary exhaust chamber 31 is closed by a cover 34 through which a rod 35 for moving a sample is inserted into the chamber 31. The table 15a on which the sample 1 is held can be coupled or attached to an end of the rod 35. A cooling block 36 is disposed in the chamber 30 which is filled with liquid nitrogen $N_2$ and is maintained to a low temperature. The cooling block 36 is provided with a heater 37 so that a temperature of the cooling block 36 can be adjusted by the heater 37. An up-and-down block 38 is disposed on the cooling block 36 and the table 15a removed from the rod 35 is placed on the block 38. A projection type optical microscope 39 is disposed above the vacuum chamber 30 and an object lens 41 of the microscope 39 is inserted in the vacuum chamber 30 and is opposed to the holder 1 in the chamber 30. The object lens 41 has a large working distance and can be maintained at a distance spaced from the holder 1 by about 10 mm. The focal distance of the object lens 41 is adjusted by up and down movement of the block 38.

A manual manipulator 42 is inserted into the vacuum chamber 30. A needle 42a is mounted to an end of the manipulator 42 through a heat isolating material 42b. The needle 42a can cut the frozen sample $X_1$ on the holder 1 more minutely. Preferably, there are provided a plurality of manipulators 42 each providing a knife, a needle, a pincette and the like, respectively. The processing process of the sample by the manipulator 42 is projected on a screen 39a of the microscope 39.

Figure 6:
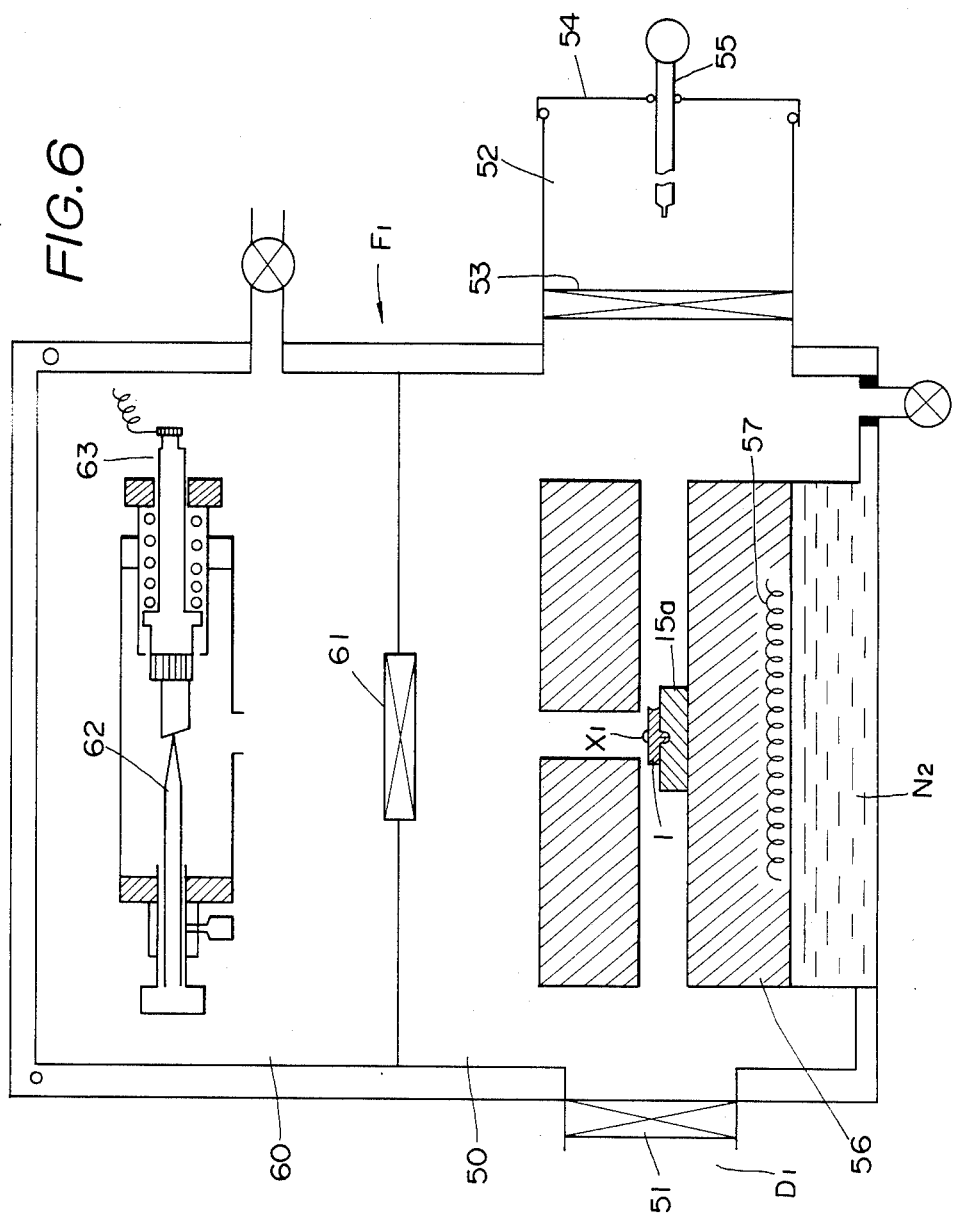
FIG. 6 is a longtiudinal sectional view of a vacuum chamber in which conductive material is coated on a sample.

FIG. 6 shows a structure of the vacuum chamber $F_1$ which is used to perform the process of coating conductive material on a sample. The vacuum chamber $F_1$ includes a vacuum chamber 50 which is separated from the operation chamber $D_1$ of the scanning electron microscope by a gate valve 51 and a preliminary exhaust chamber 52 which is separated from the vacuum chamber 50 by a gate valve 53. The preliminary exhaust chamber 52 is provided with a cover 54 through which a rod 55 for moving the sample is inserted into the chamber 52, and the table 15a is attached to an end of the rod 55. A cooling block 56 is provided in the vacuum chamber 50. The cooling block 56 is filled with liquid nitrogen $N_2$ and is provided with a heater 57 so that a temperature of the cooling block 56 can be adjusted by the heater 57. The table 15a holding the holder 1 is moved into the cooling block 56 by the rod 55.

A rod exchange chamber 60 is disposed above the vacuum chamber 50 and is separated from the vacuum chamber 50 by a gate valve 61. In the rod exchange chamber 60 there are provided a carbon rod 62 and an electrode 63 which applies a voltage to the carbon rod 62. In the vacuum chamber $F_1$, the process of coating conductive material on the sample $X_1$ can be performed by heating the carbon rod 62.

Figure 7:
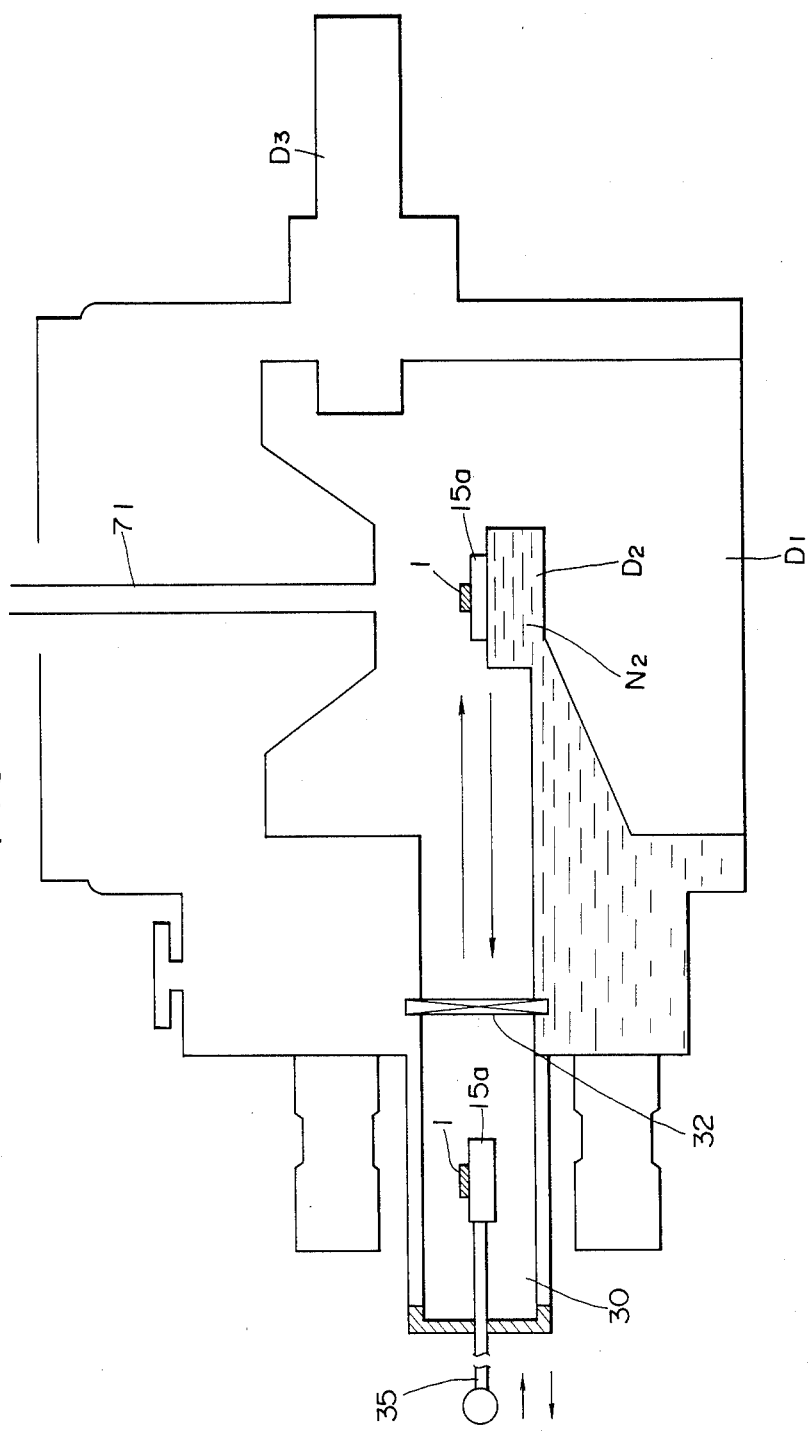
FIG. 7 is a longitudinal sectional view showing the operation chamber and a cooling stage of the scanning electron microscope.

FIG. 7 shows the operation chamber $D_1$ of the scanning electron microscope. The cooling stage $D_2$ disposed in the center of the operation chamber $D_1$ is cooled by liquid nitrogen $N_2$. Although not shown in the figure, the table 15a placed on the cooling stage $D_2$ can be adjusted from the outside so that a rotational direction and an angle thereof can be changed. The cooling stage $D_2$ is opposed to a passage 71 of a scanning electron beam. The secondary-electron detector $D_3$ faces to the operation chamber $D_1$. The vacuum chambers $B_1$, $C_1$, $E_1$ and $F_1$ are disposed radially about the cooling stage $D_2$ as shown in FIG. 2. The rods 15, 35 and 55 provided in the vacuum chambers $B_1$, $E_1$ and $F_1$, respectively, can be extended above the cooling stage $D_2$.

Figure 8:
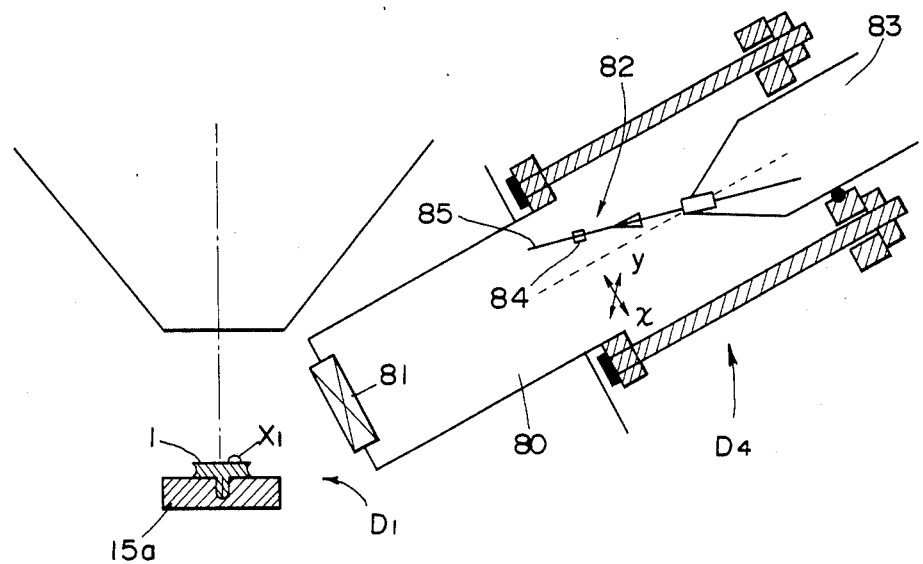
FIG. 8 is a longitudinal sectional view of micro-manipulator used for processing a sample under the scanning electron microscope.

FIG. 8 shows a structure of the micro-manipulator $D_4$. The micro-manipulator $D_4$ includes a micro-manipulator exchange chamber 80 which is separated from the operation chamber $D_1$ of the scanning electron microscope by a gate valve 81. A preliminary exhaust device not shown is provided adjacent to the exchange chamber 80. The exchange chamber 80 is provided with a micro-manipulator 82. The micro-manipulator 82 is driven by a drive mechanism 83 so that the micro-manipulator 82 can be moved forward and backward and in the x and y direction as shown in FIG. 8. The drive mechanism 83 includes a pulse motor as a power source, and can control the micro-manipulator 82 to be very small distance in accordance with operation commands supplied from a microcomputer.

Figures 9A, 9B, 9C, 9D, 9E:
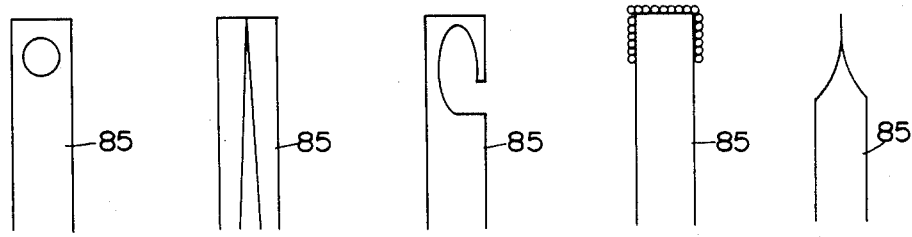
FIGS. 9A, 9B, 9C, 9D and 9E are enlarged plan views of various types of needles for the micro-manipulator, respectively.

A needle 85 is mounted to an end of the micro-manipulator 82 through a heat isolating material 84. FIGS. 9A to 9E show needles of various shapes. The needles 85 shown in the figures can be mounted to the micro-manipulator 82 if necessary. The needles 85 are formed of tungsten plated with gold. The needle shown in FIG. 9A is of a plate shape with a pin hole having a diameter of about 1 to 2 $\mu$m being formed at an end thereof. The needle of FIG. 9B is a micro-pincette. The needle of FIG. 9C is formed with an oval notch at an end thereof. The needle of FIG. 9D is a micro drill having fine particles of diamond being adhered to an end thereof. The needle of FIG. 9E is a micro needle of which an end is formed sharply.

The method of processing a sample containing water under the scanning electron microscope using the above apparatus is now described.

Figure 1:
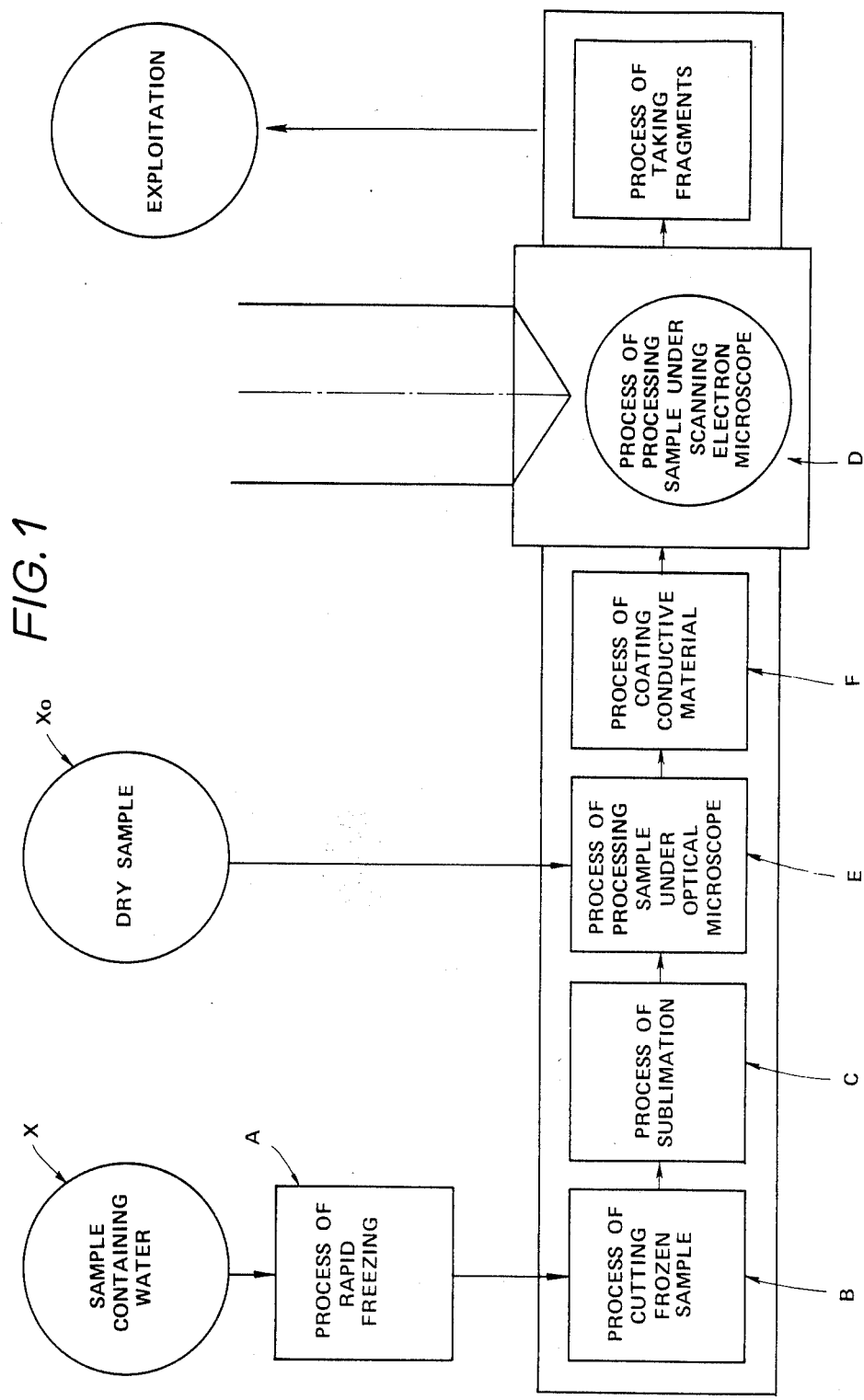
FIG. 1 illustrates a series of processes performed by a method according to the present invention.

The whole processes of the method include, as shown in FIG. 1, a process A of rapid freezing a raw sample containing water X, a process B of cutting the frozen sample under vacuum, a process C of sublimating water contained in the cut sample from its cut surface, a process E of cutting roughly the sample after sublimation by the manipulator under the optical microscope, a process F of coating conductive material on the roughly cut sample, and a process D of processing the sample by the micro-manipulator under the scanning electron microscope to extract useful fragments such as hyphae from the sample.

Each of the processes is now described in detail.

First of all, a raw sample containing water is held on the holder 1 shown in FIGS. 3A and 3B. If the sample is a suspension containing fungi, the suspension is attached on the groove 1a by surface tension. Further, if the sample is part of a plant, it is held by the holding needle 1b.

In the rapid freezing process A, the holder 1 is rapidly immersed into liquid nitrogen and the water contained sample X on the holder 1 is rapidly frozen to a low temperature of minus 210° C.

The processes B and C are performed in the vacuum chambers $B_1$ and $C_1$ shown in FIG. 4. The holder 1 holding the rapidly frozen sample $X_1$ is placed on the table 15a and is moved on the cooling block 16 of the vacuum chamber 10 by extending the rod 15. In the vacuum chamber $B_1$, the cooled cutter 17 is operated under vacuum and a low temperature and the frozen sample $X_1$ on the holder 1 is cut by the cutter 17 largely at random. The cutting operation is continuously made by rotation of the cutter 17 about a horizontal axis or a vertical axis. The cut sample $X_1$ by the cutter 17 is immediately observed through the optical microscope 19. The observation by the optical microscope 19 can cut the frozen sample $X_1$ so that useful fragment such as hyphae in the frozen sample $X_1$ are left in the cut surface. Useless fragments of the frozen sample $X_1$ are removed at the cutter process.

Then, the table 15a is moved above the heating member 21 of the vacuum chamber $C_1$ and the heater 23 is gradually heated while the cut surface of the frozen sample $X_1$ is opposed to the sublimation surface 22a with small gap between the cut surface of the sample $X_1$ and the sublimation surface 22a so that water contained in the sample $X_1$ is sublimated. In order to observe the sublimation state of the sample $X_1$, the table 15a may be moved under the optical microscope 19 again to observe the sample. In order to promote the observation, the optical microscope 19 may be disposed between the vacuum chambers $B_1$ and $C_1$.

The process E of processing the sample under the optical microscope is performed if necessary. In order to proceed to the process E, the table 15a in the vacuum chamber $C_1$ is moved to the operation chamber $D_1$ of the canning electron microscope by the rod 15 and is placed on the cooling stage $D_2$ in the operation chamber $D_1$ once. The rod 35 provided in the vacuum chamber $E_1$ of FIG. 5 is then extended to be attached to the table 15a placed on the cooling stage $D_2$ in the operation chamber $D_1$ and the table 15a is moved on the up-and-down block 38 in the vacuum chamber $E_1$. While observing the frozen sample $X_1$ on the table 15a placed on the up-and-down block 38 by the projection type microscope 39, the frozen sample $X_1$ is further cut by the manipulator 42 so that portions containing useful fragment in the sample are left and useless portions are removed.

The process F of coating conductive material on the sample is performed only when it is necessary to coat conductive material on the sample cut roughly in the process E. In the process F, after the sample has been processed in the vacuum chamber $E_1$ of FIG. 5, the table 15a is returned on the cooling stage $D_2$ in the operation chamber $D_1$ by the rod 35. Then, the table 15a is moved to the cooling block 56 by rod 55 in the vacuum chamber $F_1$ shown in FIG. 6. The gate valves 51 and 53 are closed in the vacuum chamber $F_1$ and the gate valve 61 is opened under vacuum. A voltage is applied to the carbon rod 62, and carbon particles emitted from the carbon rod 62 are coated on the frozen sample $X_1$. After completion of the process F, the table 15a is returned on the cooling stage $D_2$ in the operation chamber $D_1$ by the rod 55.

The process D of processing the sample under the scanning electron microscope is then performed. In the process D, a proper needle of those shown in FIGS. 9A to 9E is mounted to the end of the micro-manipulator 82 of FIG. 8. The exchange chamber 80 is preliminarily evacuated and the gate valve 81 is then opened. The micro-manipulator 82 is driven by a pulse motor in accordance with commands of a microcomputer to move the needle 85 onto the frozen sample $X_1$.

While observing the sample by the scanning electron microscope, useful fragments such as hyphae are extracted from the sample $X_1$ by the needle 85. The extraction is made by exchanging the needle 85 of various types shown in FIGS. 9A to 9E. For example, the surface of the sample is shaved by the needle of FIG. 9D. The needle of FIGS. 9A or 9C extracts or cuts hyphae from the sample. The micro-pincette of FIG. 9B extracts hyphae or the like. The useful fragments thus extracted from the sample is pierced by the micro-needle of FIG. 9E, is separated from the sample $X_1$ and is entered in the container 1c of the holder 1.

After completion of the above processes, the holder 1 is taken out from the operation chamber $D_1$ and the useful fragments in the container 1c of the holder are used from study and culture.

Further, as shown in FIG. 1, the processing apparatus can deal with a dry sample Xo. In this case, the dry sample Xo is moved to the process E to cut the sample by manipulator roughly under the optical microscope. After the process F of coating conductive material on the sample, the sample is moved to the process D.

As described above, according to the sample processing method under the scanning electron microscope of the present invention, since the raw sample containing water which is rapidly frozen is cut under vacuum and after sublimation useful fragments are extracted from the sample while observing the sample by the scanning electron microscope, minute useful fragments such as hyphae in the form of almost raw fragments can be extracted. Accordingly, the useful fragments can be utilized for various studies such as culture or high degree analysis.

Further, according to the sample processing apparatus using the scanning electron microscope of the present invention, the operation of extracting the useful fragments from the raw sample can be exactly attained by a series of processes.

We claim:

1. An apparatus for processing a sample using a scanning electron microscope comprising:
   an operation chamber of a scanning electron microscope, said operation chamber including a cooling stage;
   a plurality of vacuum chambers radially provided about said operation chamber, each of said vacuum chambers being provided with a gate valve means which shuts off the communication with said operation chamber and another gate valve means which shuts off the communication with a preliminary exhaust chamber provided on the other side of said gate valve means;
   a plurality of sample moving rods each of which is used to move a sample, one of said plurality of sample moving rods being provided in each of said plurality of vacuum chambers and advances from each of said plurality of vacuum chambers to said operation chamber passing through said gate valve means which is opened, and a sample holder alternatively connected to ends of said plurality of sample moving rods;
   a cutter provided in any one of said plurality of vacuum chambers which are provided radially, said cutter cutting said sample such that a useful fragment of said sample is exposed on a cutting surface as much as possible, said sample being set in said sample holder and having been rapidly frozen;
   a heating means connected to said cutter provided in said one of said plurality of vacuum chambers with said cutter, said heating means gradually heating and sublimating said sample, which has been cut by said cutter, while said sample which has been cut is placed in said sample holder;
   a manipulator means provided in any of said plurality of vacuum chambers which are provided radially, said manipulator means observing the sublimated sample and cutting said sublimated sample more finely;
   a means for coating conductive material on said sample which has been sublimated and finely cut while said sample is being set in said sample holder, said coating means being provided in any of said plurality of vacuum chambers which are provided radially; and
   a micro manipulator means extending above said cooling stage provided in said operation chamber of said scanning electron microscope for finely cutting said sample, which has been coated with conductive material and placed on said cooling stage, so that a useful fragment of said sample can be taken out and held by the sample holder.

2. An apparatus according to claim 1 wherein an optical microscope is provided in said vacuum chamber in which said cutter for cutting said rapidly frozen sample is provided so that said useful fragments can be exposed as much as possible on said cutting surface.

* * * * *